(12) United States Patent
Choi et al.

(10) Patent No.: US 9,097,719 B2
(45) Date of Patent: Aug. 4, 2015

(54) ULTRA HIGH SPEED AND HIGH SENSITIVITY DNA SEQUENCING SYSTEM AND METHOD FOR SAME

(75) Inventors: Jung Bum Choi, Cheongju-si (KR); Jong Jin Lee, Cheongju-si (KR)

(73) Assignee: NanoChips, Inc., Cheongju-si (KR)

( * ) Notice: Subject to any disclaimer, the term of this patent is extended or adjusted under 35 U.S.C. 154(b) by 1095 days.

(21) Appl. No.: 13/063,268

(22) PCT Filed: Oct. 8, 2009

(86) PCT No.: PCT/KR2009/005742
§ 371 (c)(1),
(2), (4) Date: Mar. 10, 2011

(87) PCT Pub. No.: WO2010/041875
PCT Pub. Date: Apr. 15, 2010

(65) Prior Publication Data
US 2011/0174620 A1     Jul. 21, 2011

(30) Foreign Application Priority Data
Oct. 10, 2008  (KR) .................. 10-2008-0099604

(51) Int. Cl.
*G01N 27/00* (2006.01)
*G01N 33/58* (2006.01)
(Continued)

(52) U.S. Cl.
CPC .............. *G01N 33/588* (2013.01); *B82Y 15/00* (2013.01); *C12Q 1/6869* (2013.01); *G01N 33/48721* (2013.01); *B01L 3/502761* (2013.01); *B82Y 5/00* (2013.01); *G01N 27/00* (2013.01); *G01N 27/414* (2013.01); *Y10S 436/806* (2013.01)

(58) Field of Classification Search
CPC .................................. G01N 27/00; B82Y 5/00
USPC ................... 422/82.01–82.02; 435/6.1, 287.2; 436/94, 144–151
See application file for complete search history.

(56) References Cited

U.S. PATENT DOCUMENTS

| 6,613,524 B1 * | 9/2003 | Erikson ..................... 435/6.12 |
| 2006/0086626 A1 | 4/2006 | Joyce et al. |

(Continued)

OTHER PUBLICATIONS

Schoelkopf et al., Science, vol. 280, No. 5367, pp. 1238-1242 (May 22, 1998).*

(Continued)

*Primary Examiner* — Jan Ludlow
(74) *Attorney, Agent, or Firm* — Christensen O'Connor Johnson Kindness PLLC

(57) ABSTRACT

The present system relates to a system architecture that uses a single electron transistor (SET) to analyze base sequences of deoxyribonucleic acid (DNA) at ultra high speed in real time. DNA represents the entire body of genetic information and consists of nucleotide units. There are a total of four types of nucleotides, and each nucleotide consists of an identical pentose (deoxyribose), phosphate group, and one of four types of bases (Adenine: A, Guanine: G, Cytosine: C, Thymine: T). A and G are purines having a bicyclic structure while C and T are pyrimidines having a monocyclic structure. Each has a different atomic arrangement, which signifies a different charge distribution from one another. Therefore, a system comprising a single electron transistor that is very sensitive to charges, a probe of a very small size that reacts to one nucleotide very effectively, and an extended gate that connects the SET with the probe, can be used to analyze DNA base sequences at ultra high speed in real time.

13 Claims, 6 Drawing Sheets

(51) Int. Cl.
*B82Y 15/00* (2011.01)
*C12Q 1/68* (2006.01)
*G01N 33/487* (2006.01)
*B82Y 5/00* (2011.01)
*B01L 3/00* (2006.01)
*G01N 27/414* (2006.01)

(56) References Cited

U.S. PATENT DOCUMENTS

2007/0116607 A1* 5/2007 Wang et al. .................. 422/83
2007/0178507 A1 8/2007 Wu et al.
2010/0084276 A1* 4/2010 Lindsay ........................ 205/93

OTHER PUBLICATIONS

Khanna, Vnod Kumar, "Existing and emerging detection technologies for DNA (Dexoyribonucleic Acid) finger printing, sequencing, bio- and analytical chips: A multidisciplinary development unifying molecular biology, chemical and electronics engineering", Biotechnology Advances, 2007, vol. 25, pp. 85-98 (total 14 pages).
Kim, Young-Rok et al., "Nanopore sensor for fast label-free detection of short double-stranded DNAs", Biosensors and Bioelectronics, 2007, vol. 22, pp. 2926-2931 (total 6 pages).
ISA/KR, International Search Report from priority International Application (PCT/KR2009/005742), (total 2 pages).
Shin, S.J., et al., "Room-Temperature Charge Stability Modulated by Quantum Effects in a Nanoscale Silicon Island," NANO Letters 11(4):1591-1597, Mar. 2011.
Shin, S.J., et al., "Si-Based Ultrasmall Multiswitching Single-Electron Transistor Operating at Room-Temperature," Applied Physics Letters 97(10):103101-1-103101-3, Oct. 2010.
Takahishi, Y., et al., "Silicon Single-Electron Devices and Their Applications," Proceedings of the 30th IEEE International Symposium on Multiple-Valued Logic (ISMVL), Portland, Ore., May 23-25, 2000, 10 pages.

* cited by examiner

ULTRA HIGH SPEED AND HIGH SENSITIVITY DNA SEQUENCING SYSTEM AND METHOD FOR SAME

BACKGROUND OF THE INVENTION

1. Field of the Invention

The present invention relates to deoxyribonucleic acid (DNA) sequencing method and system. More specifically, the invention relates to a method and a system for analyzing a large amount of DNA sequences in real time at ultra high speed much higher than that of the existing analysis method.

2. Background of the Related Art

DNA is the entire body of genetic information and is composed of nucleotides. Protein is synthesized based on a nucleotide sequence recorded in DNA. If the nucleotide sequence is different from the original sequence, different protein may be synthesized to generate a critical problem. Accordingly, it is very important and required to inspect whether DNA has a right nucleotide sequence in terms of disease prevention and treatment.

There are a total of four types of nucleotides, and each nucleotide consists of an identical pentose (deoxyribose), phosphate group, and one of four types of bases (Adenine: A, Guanine: G, Cytosine: C, Thymine: T). A and G are purines having a bicyclic structure while C and T are pyrimidines having a monocyclic structure.

A variety of DNA sequencing methods have been developed from early methods such as Maxam-Gilbert sequencing, Chain-Termination methods, etc. to Dye-Terminator sequencing. However, these methods analyze only a small number of bases per unit time and require a long time for a preparation work, for example, radioactive isotope substitution or dying. Furthermore, it is disadvantageous in that the methods need high cost and produce environmental pollution such as radioactive waste after analysis.

Moreover, the length of DNA which can be analyzed is limited and it is difficult to simultaneously analyze many DNAs.

DETAILED DESCRIPTION OF THE INVENTION

Subjects of the Invention

Accordingly, the present invention has been made in view of the above-mentioned problems occurring in the prior art, and it is a primary object of the present invention to provide a ultra high speed and high sensitivity DNA sequencing system and method. The two strands have complement sequences to each other, and thus the sequence of only one of the two strands may be analyzed.

Resolution of the Invention

The ultra high speed and high sensitivity DNA sequencing system and method separates DNA double helix into two strands. The two strands have complement sequences to each other, and thus the sequence of only one of the two strands may be analyzed.

Accordingly, DNA is passed through a moving part substrate in which a hole or a channel having a size through which a single nucleotide can pass is formed. Here, a very small probe is placed in the middle of the hole or channel such that the probe effectively reacts to the nearest nucleotide.

The probe is coupled to a quantum dot of a single-electron transistor through an extended gate. The quantum dot of the single-electron transistor reacts to surrounding charges very sensitively. Accordingly, the charge distribution of the probe, induced according to a base type, is transferred to the quantum dot of the single-electron transistor through the extended gate to change the conductivity of the single-electron transistor. By measuring the conductivity of the single-electron transistor, the base type reacting to the probe can be correctly detected.

To accomplish the above object of the present invention, according to an aspect of the present invention, there is provided a DNA sequencing system comprising a moving part composed of a moving part substrate in which a hole or a channel having a size through which one strand of a predetermined DNA double helix can pass is formed and a probe effectively reacting to the nearest nucleotide; a sensing part composed of a single-electron transistor electrically sensitively reacting to charges; an extended gate coupling the moving part to the sensing part.

The hole may be formed in a direction perpendicular to the surface of the substrate and a single strand of DNA may pass through the hole. The DNA may be moved through the hole from the top to bottom of the substrate or from the bottom to top of the substrate by using electrophoresis, etc. The moving part preferably has the probe made from a conductive thin film which effectively reacts to the nearest nucleotide to change charge distribution thereof.

The channel may be formed in-plane on the substrate in parallel with the surface of the substrate and have a width such that the one stand of DNA can be moved through the channel on the surface of the substrate by using electrophoresis. The probe of the moving part may be formed from a conductive thin film which effectively reacts to the nearest nucleotide to change charge distribution thereof and placed in the middle of the channel.

The single-electron transistor of the sensing part may comprise a quantum dot having a size in the range of several to tens nanometers, a source emitting an electron to the quantum dot, a drain receiving the electron from the quantum dot, a first gate controlling the state of the quantum dot, and a second gate required to couple the probe and the quantum dot to each other.

The second gate may be designed such that capacitance between the second gate and the quantum dot is maximized to effectively transfer a variation in the probe according to the nucleotide to the quantum dot of the single-electron transistor.

The single-electron transistor of the sensing part may be replaced by a quantum point contact.

The sensing part may further comprise an amplifier provided near the drain to increase a speed of measuring the conductivity of the single-electron transistor or quantum point contact.

The sensing part may further comprise a resonant circuit provided near the single-electron transistor or quantum point contact and apply an RF or microwave signal to increase charge sensitivity and analysis speed.

The DNA sequencing system may have the sensing part, the moving part and the extended gate integrated as an on-chip on a single substrate to maximize a signal transfer rate.

When it is required to decrease the temperature of the sensing part such that charge sensitivity and operation characteristics of the sensing part can be improved, the sensing part and the moving part may be respectively formed on different substrates. By doing so, the temperature of only the sensing part substrate can be selectively decreased. The DNA sequencing system may couple the second gate of the sensing part to the probe of the moving part by using a metal wire as the extended gate in consideration of thermal conductivity and signal transmission characteristic.

The moving part may include a dielectric layer formed on the inner surface of the hole or channel through which the DNA is moved such that the probe and nucleotide react to each other through the dielectric layer.

The moving part may not include the dielectric layer formed on the inner surface of the hole or channel through which the DNA is moved such that the probe and nucleotide directly react to each other.

The DNA sequencing system may include multiple probes formed at intervals in the hole perpendicular to the surface of a moving part substrate or in the channel parallel with the surface of the moving part substrate and single-electron transistors as many as the number of probes, formed on a sensing part substrate and respectively coupled to the probes. Accordingly, a single DNA can be analyzed multiple times through one-time analysis work. Furthermore, analysis and inspection can be simultaneously performed to eliminate analysis error.

The DNA sequencing system may include multiple holes or multiple channels formed in the moving part substrate and single-electron transistors as many as the number of probes formed on the moving part substrate, which are formed on the sensing part substrate and respectively coupled to the probes through the extended gate, so as to simultaneously analyze multiple DNAs.

To accomplish the above object of the present invention, according to another aspect of the present invention, there is provided a DNA sequencing method which couples a probe, which has a charge distribution varied with a charge distribution difference between different bases of DNA, to an element sensitively reacting to charges (for example, a single-electron transistor or a quantum point contact) to measure a variation in the conductivity of the element to detect the types of the bases.

Effects of the Invention

The DNA sequencing method and system proposed, by the present invention does not require an additional preparation operation other than the operation of separating DNA double helix into two strands, and thus the sequencing work is simplified. Furthermore, materials such as radioactive isotopes or dyes are not discharged and a large quantity of DNAs can be simultaneously analyzed at ultra high speed in real time in an automated manner irrespective of DNA length. Moreover, inspection can be performed simultaneously with analysis, and thus analysis error can be prevented.

BRIEF DESCRIPTION OF THE DRAWINGS

The above and other objects, features and advantages of the present invention will be apparent from the following detailed description of the preferred embodiments of the invention in conjunction with the accompanying drawings, in which.

DESCRIPTION OF REFERENCE NUMERALS OF PRINCIPAL ELEMENTS IN THE DRAWINGS

Figure 1:
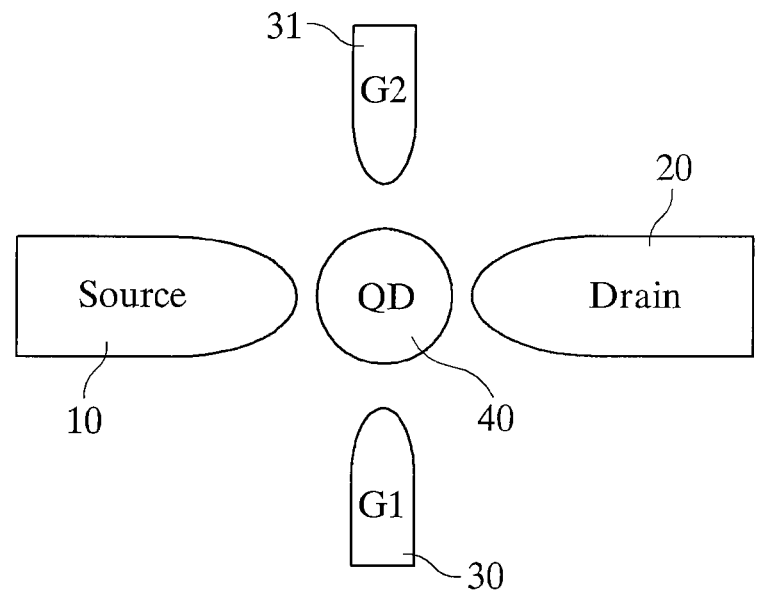
FIG. 1 illustrates a structure of a conventional single-electron transistor.

10, S: source
20, D: drain
30, G1: first gate
31, G2: second gate
40: quantum dot
100: moving substrate
110: probe
200: Deoxyribonucleic acid (DNA)
300: extended gate

DETAILED DESCRIPTION OF THE PREFERRED EMBODIMENT (Configuration)

Figure 2:
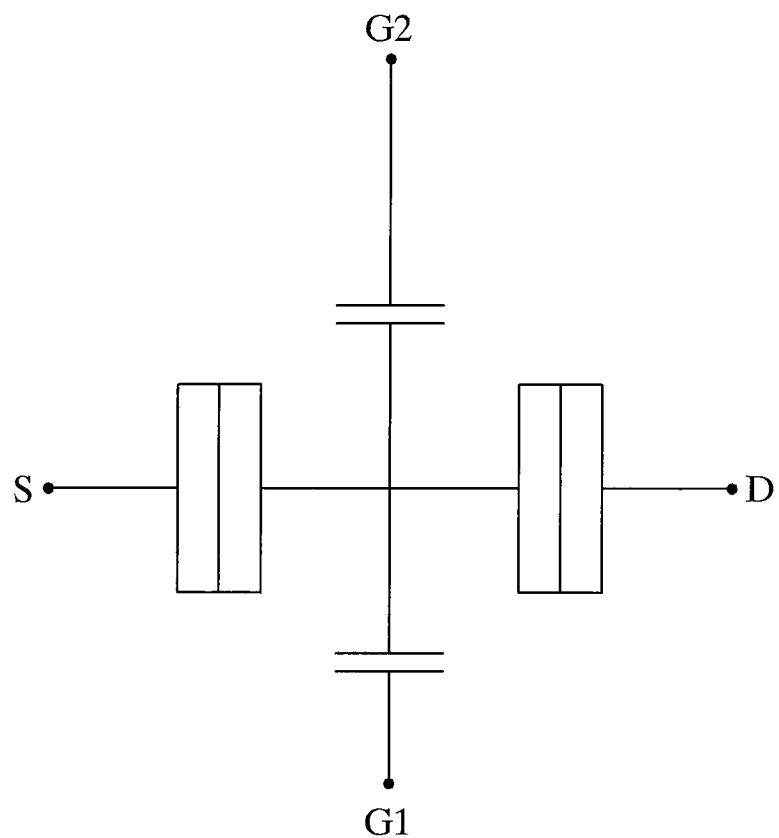
FIG. 2 is a circuit diagram of the conventional single-electron transistor.

FIG. 1 illustrates a structure of a conventional single-electron transistor and FIG. 2 is a circuit diagram schematically showing a constitution of the conventional single-electron transistor. The single-electron transistor shown in FIGS. 1 and 2 is used for a sensing part of the present invention. Referring to FIGS. 1 and 2, the single-electron transistor includes a quantum dot QD 40 having a size in the range of several to tens nanometers, a source S 10 emitting an electron to the quantum dot QD 40, a drain D 20 receiving the electron from the quantum dot QD 40, a first gate G1 30 controlling the state of the quantum dot QD 40, and a second gate G2 31 required for coupling a probe to the quantum dot QD 40.

The single-electron transistor may be replaced by an element that sensitively reacts to charges, such as quantum point contact QPC, and an amplifier may be provided near the element to improve the reaction speed of the element. To increase charge sensitivity in addition to the reaction speed, a resonant circuit and RF or microwave signals may be used or the operating temperature of the element may be decreased.

Figure 3:
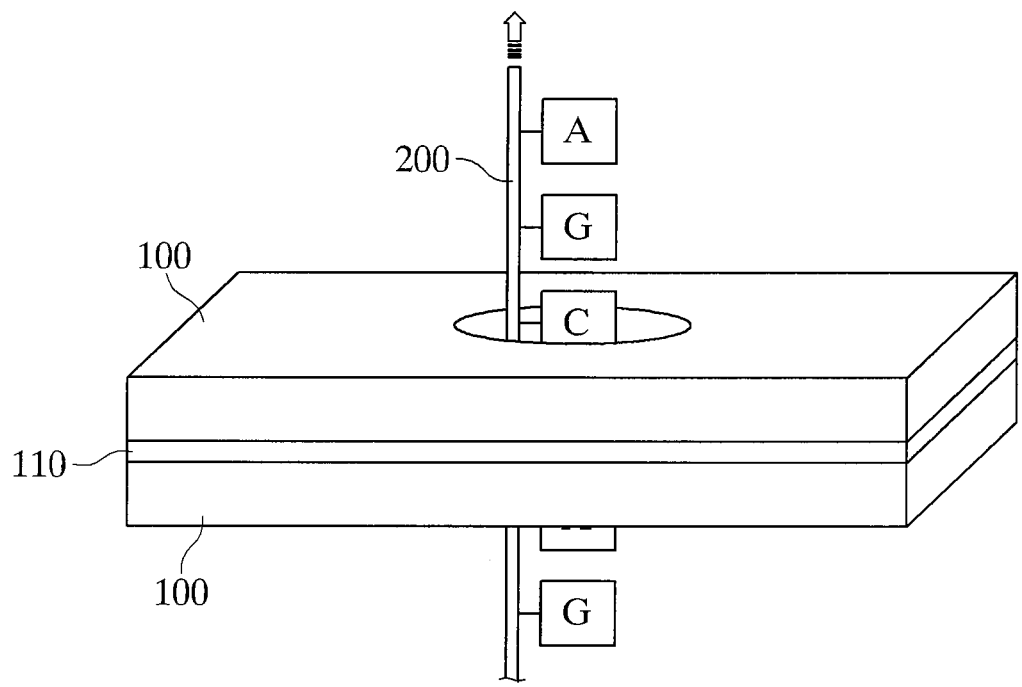
FIG. 3 is a perspective view showing a state of moving DNA through a vertical moving part having a hole formed in a substrate in a vertical direction according to a first embodiment of the present invention.
Figure 4:
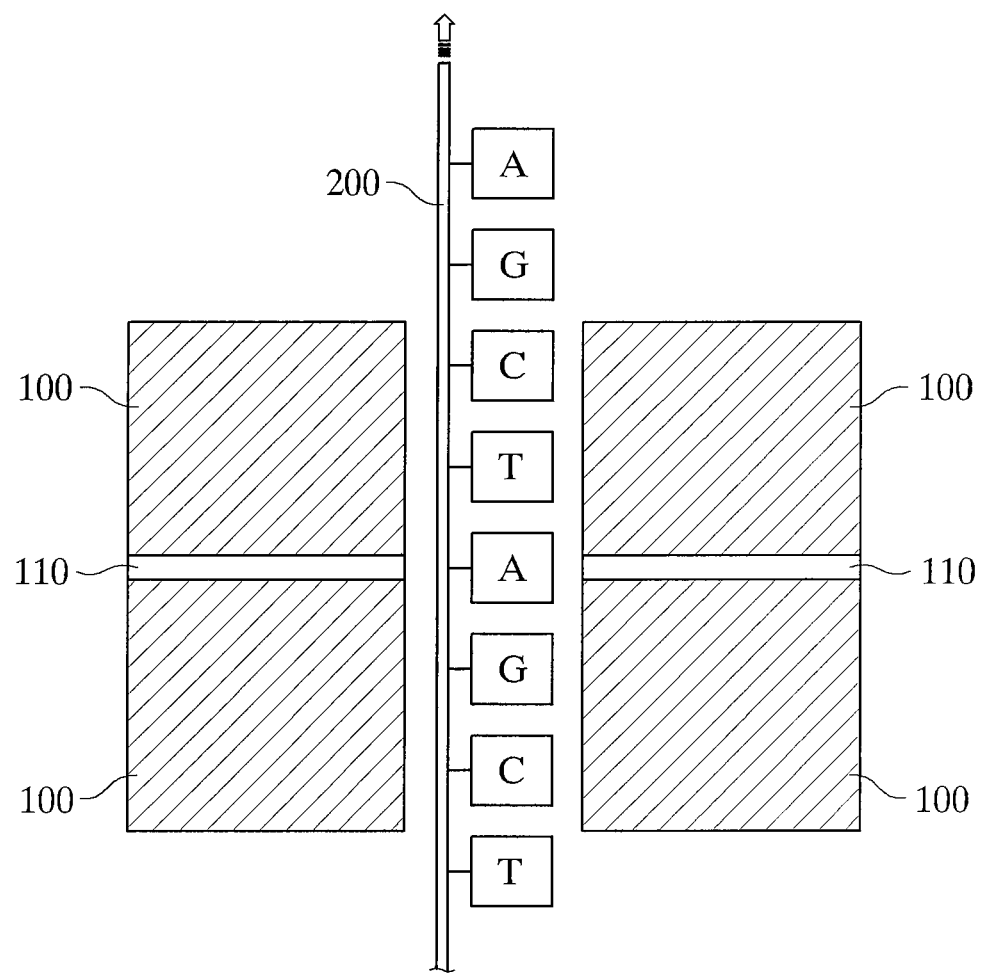
FIG. 4 is a cross-sectional view showing the upper and lower pats of the hole formed in the substrate shown in FIG. 3.

FIG. 3 is a perspective view showing a state of moving DNA through a vertical moving part having a hole formed in a substrate in a vertical direction according to a first embodiment of the present invention and FIG. 4 is a cross-sectional view showing the upper and lower pats of the hole formed in the substrate shown in FIG. 3. Referring to FIGS. 3 and 4, the moving part includes a moving part substrate 100 in which a hole having a size through which one strand of a predetermined DNA double helix 200 can pass is formed and a probe 110 that is provided in the middle of the hole and reacts to the nearest nucleotide.

That is, the DNA 200 is passed through the hole having a size through which a single nucleotide can pass and the very small probe 110 effectively reacting to the nearest nucleotide is placed in the middle of the hole.

On the basis of this structure, multiple probes may be set in a single hole to simultaneously perform analysis and inspection or multiple holes may be formed in a single substrate to simultaneously analyze multiple DNAs.

Here, a sensing part (not shown) may be composed of a single-electron transistor capable of measuring a conductivity variation based on the charge distribution of the probe 110, which is varied according to reaction to the DNA 200, and coupled to the probe 110 through an extended gate. Here, the single-electron transistor may be integrated as an on-chip on the moving part substrate 100 or separately formed on a substrate different from the moving part substrate 100.

A DNA sequencing method according to the first embodiment of the present invention separates the DNA double helix 200 into two strands and analyzes the sequence of one of the two strands since the two strands have complement sequences to each other. The sequencing method will be described later.

Figure 5:
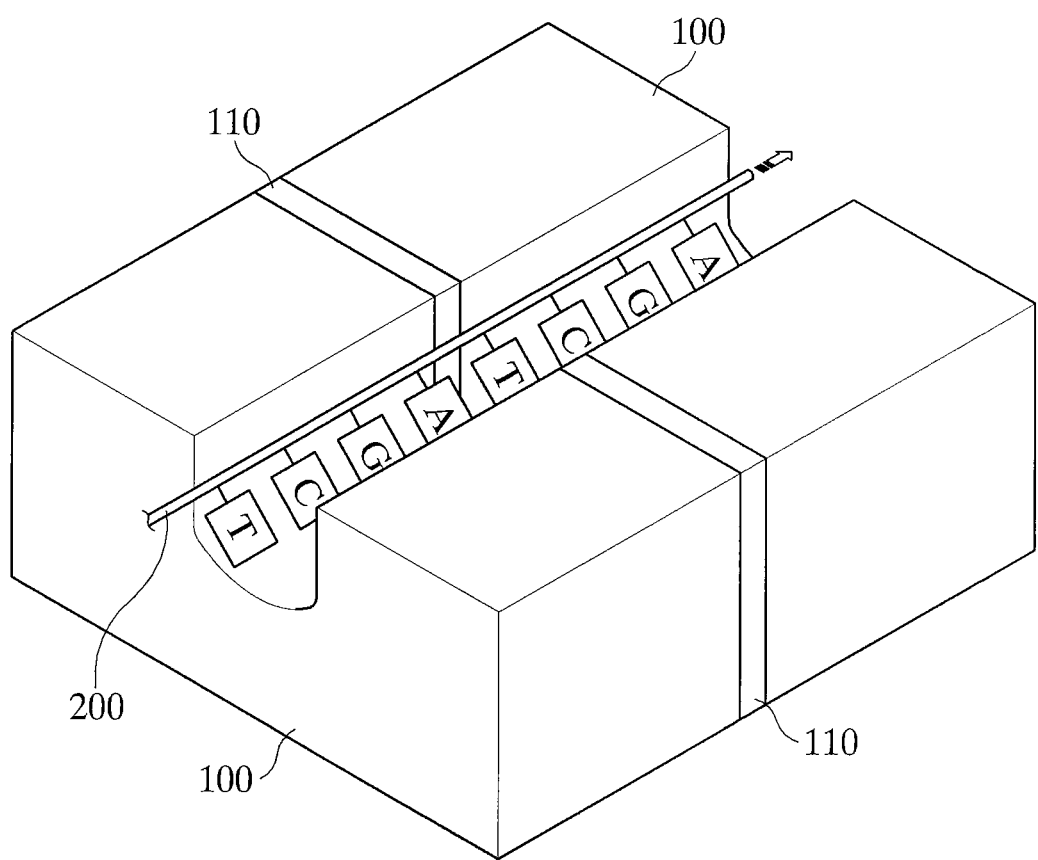
FIG. 5 is a perspective view showing a state of moving DNA through a horizontal moving part having a channel formed on a substrate in a horizontal direction according to a second embodiment of the present invention.

FIG. 5 is a perspective view showing a state of moving DNA through a horizontal moving part having a channel formed on a substrate in a horizontal direction according to a second embodiment of the present invention. Referring to FIG. 5, the moving part includes the moving part substrate 100 on which the channel having a size through which one strand of a predetermined DNA double helix 200 can pass is formed and the probe 110 that is provided in the middle of the channel and reacts to the nearest nucleotide.

That is, DNA 200 is passed through the channel having a size through which a single nucleotide can pass and the very small probe 110 effectively reacting to the nearest nucleotide is placed in the middle of the channel.

On the basis of this structure, multiple probes may be set in a single channel to simultaneously perform analysis and inspection or multiple channels may be formed on a single substrate to simultaneously analyze multiple DNAs.

Figure 6:
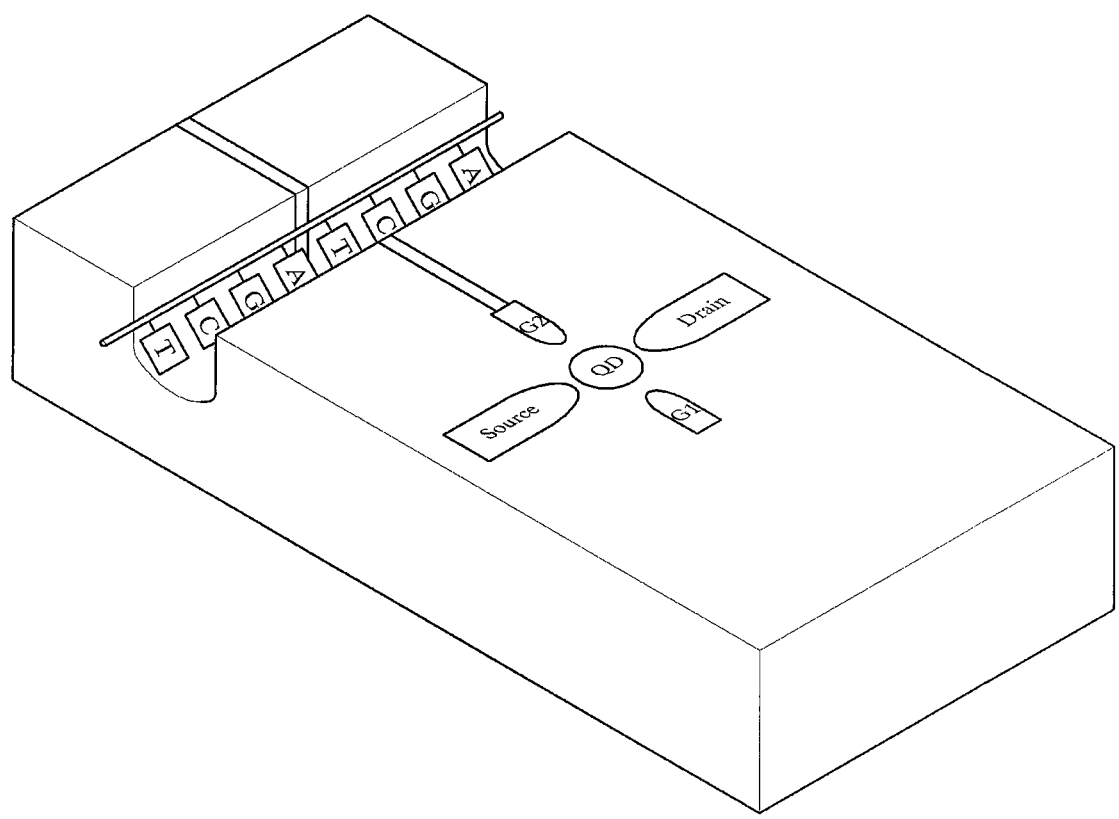
FIG. 6 is a three-dimensional view showing coupling of a probe of a horizontal moving part and a single-electron transistor of a sensing part, which are integrated in a single substrate, through an extended gate according to a third embodiment of the present invention.

FIG. 6 is a three-dimensional view showing a system including the probe of the horizontal moving part and the single-electron transistor of the sensing part, which are integrated in the single substrate and coupled to each other through an extended gate, according to a third embodiment of the present invention. Referring to FIG. 6, the moving part includes the moving part substrate 100 and the probe 110 and the single-electron transistor (or sensing part) includes the source 10, the drain 20, the first gate 30, and the second gate 31. The extended gate is integrated as an on-chip on the substrate 100 to maximize a signal transmission speed.

Here, the sensing part is composed of the single-electron transistor capable of measuring conductivity variation based on the charge distribution of the probe 110, which is varied according to reaction to DNA 200, and the extended gate couples the moving part and the sensing part to each other.

Figure 7:
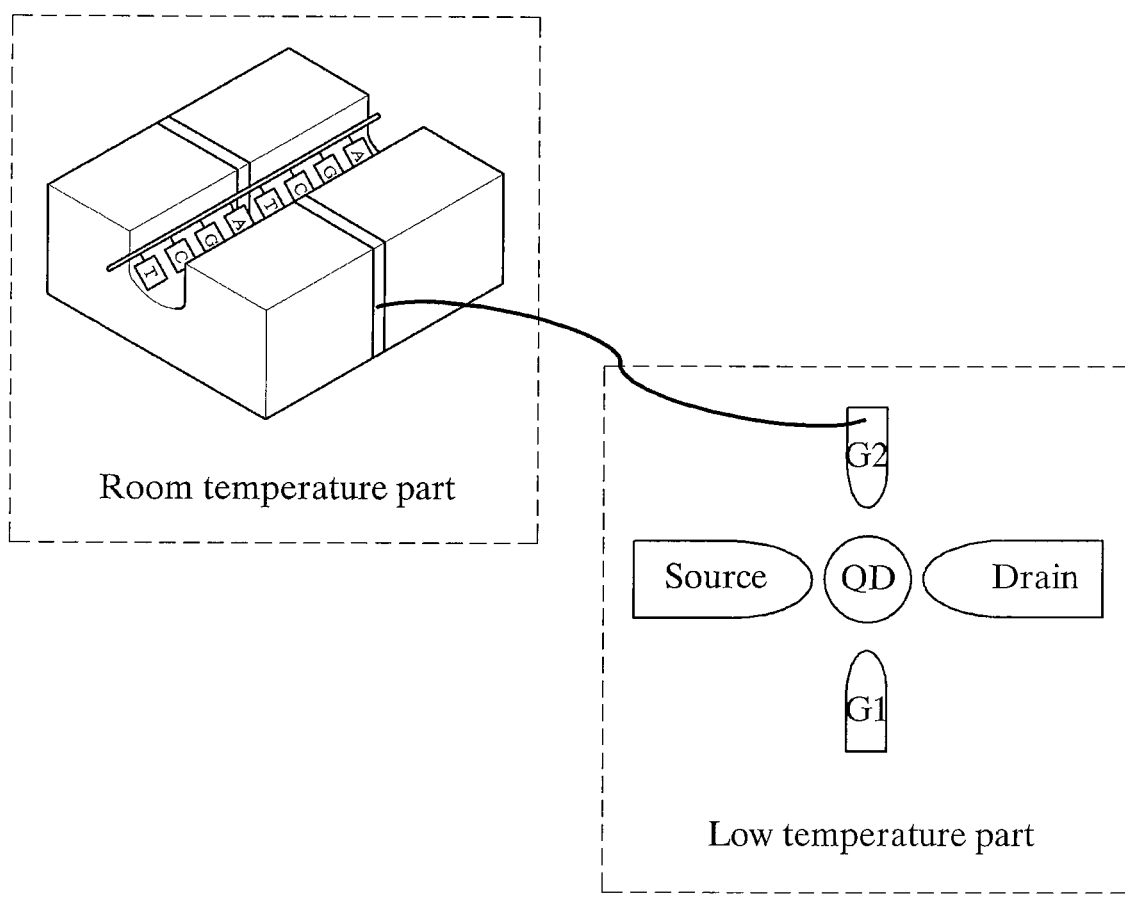
FIG. 7 is a three-dimensional view showing coupling of a probe of a horizontal moving part and a single-electron transistor of a sensing part, which are respectively formed on different substrates, through an extended gate according to a fourth embodiment of the present invention.

FIG. 7 is a three-dimensional view showing coupling of a probe of a horizontal moving part and a single-electron transistor of a sensing part, which are respectively formed on different substrates, through an extended gate 300 according to a fourth embodiment of the present invention. Referring to FIG. 7 the sensing part and the moving part may be respectively formed on a sensing part substrate and a moving part substrate to reduce the temperature of the sensing part so as to increase the charge sensitivity and operating characteristic of the sensing part. The extended gate uses a metal-wire extended gate 300 that connects the second gate 31 and the probe 110 to decrease thermal conductivity and increase signal transfer characteristic.

(Sequencing Method)

DNA double helix is separated into two strands. The two strands have complement sequences to each other, and thus the sequence of only one of the two strands is analyzed using the ultra high speed and high sensitivity DNA sequencing system of the present invention.

The probe has a charge distribution variation according to the nearest nucleotide changing as predetermined DNA moves through the hole or channel formed in the moving part substrate, in S10. Here, the DNA may be moved through the hole or channel from the top to bottom of the substrate or from the bottom to top of the substrate using electrophoresis, etc.

In S20, the extended gate 300 transfers varied charge distribution of probe to the quantum dot 40 of the single-electron transistor. The quantum dot 40 of the single-electron transistor reacts to surrounding charges remarkably sensitively, thus this transfer results in a significant variation in the conductivity of the single-electron transistor.

Here, in S30, a predetermined analyzer (not shown) may analyze the conductivity of the single-electron transistor to correctly detect the base type reacting to the probe 110.

What is claimed is:

1. A DNA sequencing system comprising:
    a moving part formed on a moving part substrate configured to operate at room temperature and having a hole or a channel, wherein the hole or channel has a size through which one strand of a predetermined DNA double helix can move and a conductive thin film in the substrate for reacting to the nearest nucleotide;
    a sensing part formed on a separate sensing part substrate configured to operate at low temperatures for improving charge sensitivity and operating characteristics of the sensing part and comprising a single-electron transistor capable of measuring a conductivity variation of the single-electron transistor based on the charge distribution of the conductive thin film, said charge distribution varying according to electrical reaction between the conductive thin film and the nearest nucleotide;
    wherein the single-electron transistor comprises:
        a quantum dot having a size in the range of several to tens nanometers;
        a source emitting an electron to the quantum dot;
        a drain receiving the electron from the quantum dot;
        a first gate controlling the state of the quantum dot;
        a second gate for controlling the state of the quantum dot; and
    an extended gate comprising a metal wire to couple the conductive thin film in the moving part to the second gate in the sensing part, wherein the extended gate reduces thermal conductivity between the substrates and increases signal transfer characteristics between the substrates.

2. The DNA sequencing system of claim 1, wherein the moving part substrate has top and bottom surfaces, the hole is formed in a direction perpendicular to the top and bottom surfaces of the moving substrate, and the conductive thin film is formed such that the charge distribution of the conductive thin film is varied by the nearest nucleotide.

3. The DNA sequencing system of claim 2, wherein a dielectric layer is formed on the inner surface of the hole such that the conductive thin film and the nucleotide react to each other through the dielectric layer.

4. The DNA sequencing system of claim 1, wherein the channel is formed in the moving part substrate in a plane parallel with surfaces of the moving part substrate, and the conductive thin film is formed such that the charge distribution of the conductive thin film is varied by the nearest nucleotide.

5. The DNA sequencing system of claim 4, wherein a dielectric layer is formed on the inner surface of the channel such that the conductive thin film and the nucleotide react to each other through the dielectric layer.

6. The DNA sequencing system of claim 1, wherein the sensing part further comprises an amplifier provided near the single-electron transistor to increase a speed of measuring the conductivity of the single-electron transistor.

7. The DNA sequencing system of claim 1, wherein the sensing part further comprises a resonant circuit provided near the single-electron transistor to increase charge sensitivity and analysis speed, and an RF or microwave signal is applied through the resonant circuit to measure reflectivity or transmissivity of the RF or microwave signal.

8. The DNA sequencing system of claim 1, wherein the conductive thin film includes a plurality of conductive thin films formed at intervals between both ends of the hole or channel to analyze and inspect the DNA multiple times through one-time analysis, the single-electron transistor includes a plurality of single-electron transistors as many as the number of the plurality of conductive thin films, formed on the separate sensing part substrate, and wherein the extended gate includes a plurality of extended gates, each extended gate connecting each one of the single-electron transistors to its respective corresponding conductive thin film connected via the extended gate.

9. The DNA sequencing system of claim 1, wherein the hole or the channel includes multiple holes or multiple channels, the conductive thin film includes multiple conductive thin films respectively corresponding to the holes or channels, the single-electron transistor includes multiple single-electron transistors which are formed on the sensing part substrate, and the single-electron transistors on the sensing part substrate are connected to their respective conductive thin films on the moving part substrate via corresponding respective extended gates.

10. The DNA sequencing system of claim 1, wherein the conductive thin film is disposed between two surfaces of the substrate.

11. The DNA sequencing system of claim 1, wherein the conductive thin film is disposed below surface of the moving part substrate.

12. A DNA sequencing method comprising:
providing separate moving and sensing substrates;
operating the moving substrate at room temperature and operating the sensing substrate at lower temperatures;
providing the moving substrate with a conductive thin film having a charge distribution that varies according to the base of a predetermined DNA, said moving substrate having a predetermined hole or a predetermined channel;
moving the predetermined DNA through the hole or chamber in the moving substrate;
providing an extended gate between the moving substrate and the sensing substrate, said extended gate coupled at one end to the conductive thin film on the moving substrate and to the sensing substrate;
on the sensing substrate, providing a single-electron transistor or a quantum point contact coupled to the extended gate so that the charge distribution variation of the conductive thin film is coupled to the single electron transistor or the quantum point contact; and
analyzing the conductivity of the single electron transistor or the quantum point contact to detect the type of base varying the charge distribution on the conductive film.

13. The DNA sequencing method of claim 12, wherein the conductive thin film is disposed below surface of the moving substrate.

* * * * *